United States Patent [19]
Varon et al.

[11] Patent Number: 5,523,238
[45] Date of Patent: Jun. 4, 1996

[54] METHOD AND APPARATUS FOR DETERMINING PLATELET FUNCTION IN PRIMARY HEMOSTASIS

[75] Inventors: David Varon, Kfar Bilu A'; Naphtali Savion, Givat Shmuel, both of Israel

[73] Assignee: Ramot University Authority for Applied Research and Industrial Development Ltd., Tel Aviv, Israel

[21] Appl. No.: 273,549

[22] Filed: Jul. 11, 1994

[30] Foreign Application Priority Data

Jul. 14, 1993 [IL] Israel ................................ 106330

[51] Int. Cl.⁶ .................................................. G01N 33/86
[52] U.S. Cl. ........................ 436/69; 436/63; 422/73; 422/99; 422/102; 435/2; 435/287.9; 435/288.1
[58] Field of Search ........................... 436/63, 69, 164, 436/177; 422/73, 99, 101, 102; 435/2, 291, 296, 312, 316

[56] References Cited

U.S. PATENT DOCUMENTS 4,880,788  11/1989  Moake et al. ........................ 514/150

OTHER PUBLICATIONS

Riess et al., *American Journal of Clinical Pathology*, vol. 85, No. 1, pp. 50–56, Jan. 1986.
Tippe et al. *Thrombosis Research*, vol. 67, No. 4, pp. 407–418, 1992.
Born, *Nature*, vol. 194, pp. 927–929, Jun. 9, 1962.
Fukuyama et al., *Thrombosis Research*, vol. 54, No. 3, pp. 253–260, 1989.
Ikeda et al., *Journal of Clinical Investigation*, vol. 87, pp. 1234–1240, Apr. 1991.
Lavee et al., *Journal of Thoracic+Cardiovascular Surgery*, vol. 97, No. 2, pp. 204–212, Feb. 1989.

Primary Examiner—Robert J. Warden
Assistant Examiner—Maureen M. Wallenhorst
Attorney, Agent, or Firm—William C. Gerstenzang; Sprung Horn Kramer & Woods

[57] ABSTRACT

A method for determining a platelet function in a primary hemostasis is provided in which a blood sample or a platelet containing fraction thereof is introduced into a vessel having a flat bottom which has an inner surface covered with a substrate capable of inducing platelet adhesion thereto and aggregation such as ECM (extracellular matrix). Preparation is then rotated inside the vessel, and consequently shear forces develop on the surface which bring to adhesion an aggregation of the blood platelets to the surface. Morphological parameters of blood aggregates are then determined.

11 Claims, 14 Drawing Sheets

FIG. 5 AFIBRINOGENEMIA

METHOD AND APPARATUS FOR DETERMINING PLATELET FUNCTION IN PRIMARY HEMOSTASIS

FIELD OF THE INVENTION

The present invention concerns a method and an apparatus for determining platelet function in primary hemostasis.

BACKGROUND OF THE INVENTION

Hemostasis, i.e. the arrest of hemorrhage, is a mechanism which comprises essentially two consecutively functioning mechanisms: "primary hemostasis" is responsible for the immediate arrest of hemorrhage and is caused by the localization and aggregation of circulating platelets on damaged vascular surfaces or exposed tissues and subsequent formation of a thrombus; "secondary hemostasis" is responsible for the long-term arrest of hemorrhage and is caused by a chain of enzymatic reactions resulting eventually in the formation of fibrin.

Abnormalities of primary hemostasis are clinical conditions associated with bleeding tendencies which can become life-threatening in traumatic situations such as operation, delivery, invasive diagnostic and therapeutic procedures as well as traumatic injury. The evaluation of the degree of primary hemostasis is thus of a high clinical importance.

Several procedures have been hitherto employed in order to evaluate primary hemostasis. One procedure termed "the bleeding time test", which is the most common clinical test for determining primary hemostasis, is carried out by inducing a controlled cut in the arm of the tested subject and determining the duration before bleeding is arrested. This procedure has relatively low clinical relevance as it is able to identify only severe abnormalities in primary hemostasis and is thus unable to distinguish between normal subjects and those whose primary hemostasis is slightly defective. Furthermore, this method is virtually impossible to standardize since the duration of bleeding depends strongly on the precise size and location of the cut as well as on the venus and arterial blood pressures.

Platelet aggregation studies are usually performed in platelet-rich plasma (PRP) using a turbidometric device according to Born (Born G. V. R., *Nature*, 194, 927–929 (1962)). One drawback of turbidometric aggregometry is that the use of PRP necessitates centrifugation and separation of platelets from other blood cells which manipulation may alter platelets' properties and behavior. Another drawback of the turbidometric method is in that it is time consuming and laborious. Finally, the evaluation of such a test is limited by the optical quality of PRP which is affected by the levels of lipids in the plasma.

Platelets' aggregation was also tested in whole blood (WB) (Riess H., *Am. J. Clin. Pathol*, 85, 50–56, (1986)). According to this technique, platelet aggregation was measured by an increase in impedence across two electrodes placed in the blood sample. However, in this technique as well as the turbidometric technique described above, the platelets' aggregation was induced by artificial reagents and consequently the conditions in which the aggregation was measured were clearly non-physiological.

Several other procedures involved subjecting PRP to shear forces and determining platelet aggregation under these conditions. The shear forces in such tests were induced either by a cone-plate apparatus in which a rotating member was rotated within a cylindrical vessel, or by various sophisticated means adapted to produce a continuous flow of fluids (Tippe A. et al., *Thrombosis Res.*, 67:407–418 (1992); Ikeda et al., *J. Clin. Invest.*, 87, 1234–1240 (1991)); Fukiyama M. et al., *Thrombosis Res.* 64:253–260 (1989)). In such tests, which were generally conducted with PRP, the shear induced adhesions took place on the surfaces of the test vessel. The physiological significance of adhesion of platelets to artificial matrix under such conditions is questionable and this procedure indeed very often fails to provide clinically significant results. In addition, the means to produce the shear force in some of the procedures disclosed in the above publications were often complicated and expensive rendering the procedure unsuitable as a routine clinical procedure.

Another hitherto disclosed procedure involved determining adhesion of platelets, in a platelet rich plasma (PRP) (Vlodavksy, I. et al., *Thrombosis Research*, 18, 179–191, (1983)) and in whole blood (Lavee J. et a., *The Journal of Thoracic and Cardiovascular Surgery*, 97, (2), 204–212, (1989)) to an extracellular matrix (ECM).

It is the object of the invention lo provide a novel method and apparatus for evaluating platelets' function in primary hemostasis.

GENERAL DESCRIPTION OF THE INVENTION

The present invention provides a method for determining platelet function in primary hemostasis comprising:

(a) obtaining a sample being whole-blood or a platelet-containing fraction thereof; and optionally mixing it with an anti-coagulant in an amount sufficient to inhibit blood coagulation;

(b) introducing the sample obtained in (a) into a vessel having a flat bottom the inner surface of which is covered with a substrate capable of inducing platelet adhesion thereto and aggregation;

(c) rotating said preparation inside the vessel, whereby shear forces develop at said surface; and (d) determining parameters of the adhered blood platelets, the parameters being selected from the group consisting of amount of adhered platelets aggregate size, aggregates' morphology, total area covered by the aggregates and distribution of adhered platelets or aggregates and or said substance.

Said substrate may be extracellular matrix (ECM), an active component thereof or any other natural or artificially produced substrates capable of inducing platelet adhesion thereto and aggregation.

ECM is a matrix produced by endothelial cells such as corneal or vascular endothelial cells usually obtained from bovine or human sources. The ECM may be produced by culturing the cells inside said the vessel and then removing the cells after production of the ECM (Gospodarowicz D., et al., *Endocr. Rev.*, 1, 201–207 (1980)). In addition, rather than using ECM, the surface may also be covered by various components thereof or artificially produced analogs which are capable of inducing the primary hemostasis, such as basement membrane matrix (e.g. MATRIGEL™, Flow Laboratories Inc., U.S.A.; Kleinman H., et al., *Biochemistry*, 25, 312–318 (1986)), fibrilar anti non-fibrilar collagen of various types, von Willebrand factor, fibronectin, etc.

In the following description the invention will be described at times with the reference to the use of ECM, it being understood that this is done for the sake of convenience only and other matrices, e.g. such consisting of said active component or analogs may equally be used.

The tested blood sample may be whole blood, i.e. blood including all its cellular components, or may be a platelet rich plasma (PRP). The sample is optionally mixed with an anti-coagulant which is added in order to neutralize the effects of the secondary hemostasis mechanism. The anti-coagulant can be any anti-coagulants known in the art, such as trisodium citrate, hirudin, heparin, etc.

The rotation of the fluid inside the vessel, and hence the shear forces, can be induced by a number of means. In accordance with one embodiment of the invention, the shear forces are produced by rotation of the vessel. In accordance with another embodiment, which is preferred in accordance with the present invention, the vessel is stationary and the rotation of the fluid is produced by a rotating element inside the vessel. The vessel in accordance with this embodiment is preferably cylindrical.

The rotating element according to the second embodiment of the invention is preferably cylindrical. In such a case, the shear forces acting on the platelets gradually increase from the center of the vessel towards the periphery. This embodiment is useful, for example, when it is desired to evaluate, in a single test, the primary hemostasis under varying shear force conditions. The difference between platelet adhesion and aggregation at the center of the ECM covered surface, where shear forces are in such a case relatively low, and the periphery where shear forces are relatively higher, can provide an indication of differences in platelet function in primary hemostasis in various blood vessels in which the platelets are subjected to different shear forces.

The rotating element has preferably a bottom portion having the shape of an inverted cone. e.g. a "cone-plate" device (Ikeda et al., *J. Clin. Invest.*, 87, 1234–1240 (1991)). In such a device the bottom, sloped faces of the cone are made at an angle, e.g. up to about 3° from horizontal, which is calculated to essentially neutralize the effect of the difference in velocity of fluid rotated by the element between its center and the periphery, and thus the shear forces produced on the ECM covered bottom surface of the vessel are essentially equal throughout the entire surface (with the exception of the very periphery due to borderline conditions which exist there). Thus, according to this embodiment, the adhesion and aggregation of platelets to the ECM covered surface are a result of an essentially uniform shear force acting on the platelets regardless of their position.

After the blood sample is placed within the vessel, the blood is rotated for a duration of 10 seconds to 10 mins., e.g. about 2 min., at a shear force of, which may for example be, in the range of 50–3000 $sec^{-1}$, preferably in the range of 100–2000 $sec^{-1}$.

The adhesion and aggregation of platelets onto the ECM is determined by any of a number of means known per se such as optical inspection using a light microscope after appropriate staining, by the use of a scanning electron microscope, determining changes in light absorbance or transmission, etc. The determination may also involve image analysis using various image analysis systems (IAS).

The present invention also provides an apparatus for carrying out the method in accordance with the above preferred embodiment of the invention. The apparatus comprises a flat bottomed vessel, and a rotating element within the vessel. The inner surface of the bottom of the vessel is covered with said substrate.

In accordance with a preferred embodiment, the rotating element has a bottom portion having the shape of an inverted cone as described above.

The rotating element in the apparatus may be driven by a number of means, e.g. by direct mechanical coupling to a rotating motor or by means of magnetic coupling to an external magnetic driving means ("magnetic stirrer").

The present invention thus provides means for evaluating primary hemostasis in a manner which will yield results which have a physiological significance, as the condition in which the adhesion and aggregation of the platelets is induced, closely resemble physiological conditions prevailing in the blood vessel. Furthermore, the invention may be carried out by the use of relatively simple and inexpensive instrumentation.

The present invention is suitable for determining both clinical situations of low function of the primary hemostasis, giving rise to risks of hemorrhages, as well as cases of pathologically high rate of primary hemostasis, which increase the risk of thrombosis.

The invention will now be described by some non-limiting embodiments with occasional reference to the annexed drawings.

DESCRIPTION OF SPECIFIC EMBODIMENTS

Figure 1:
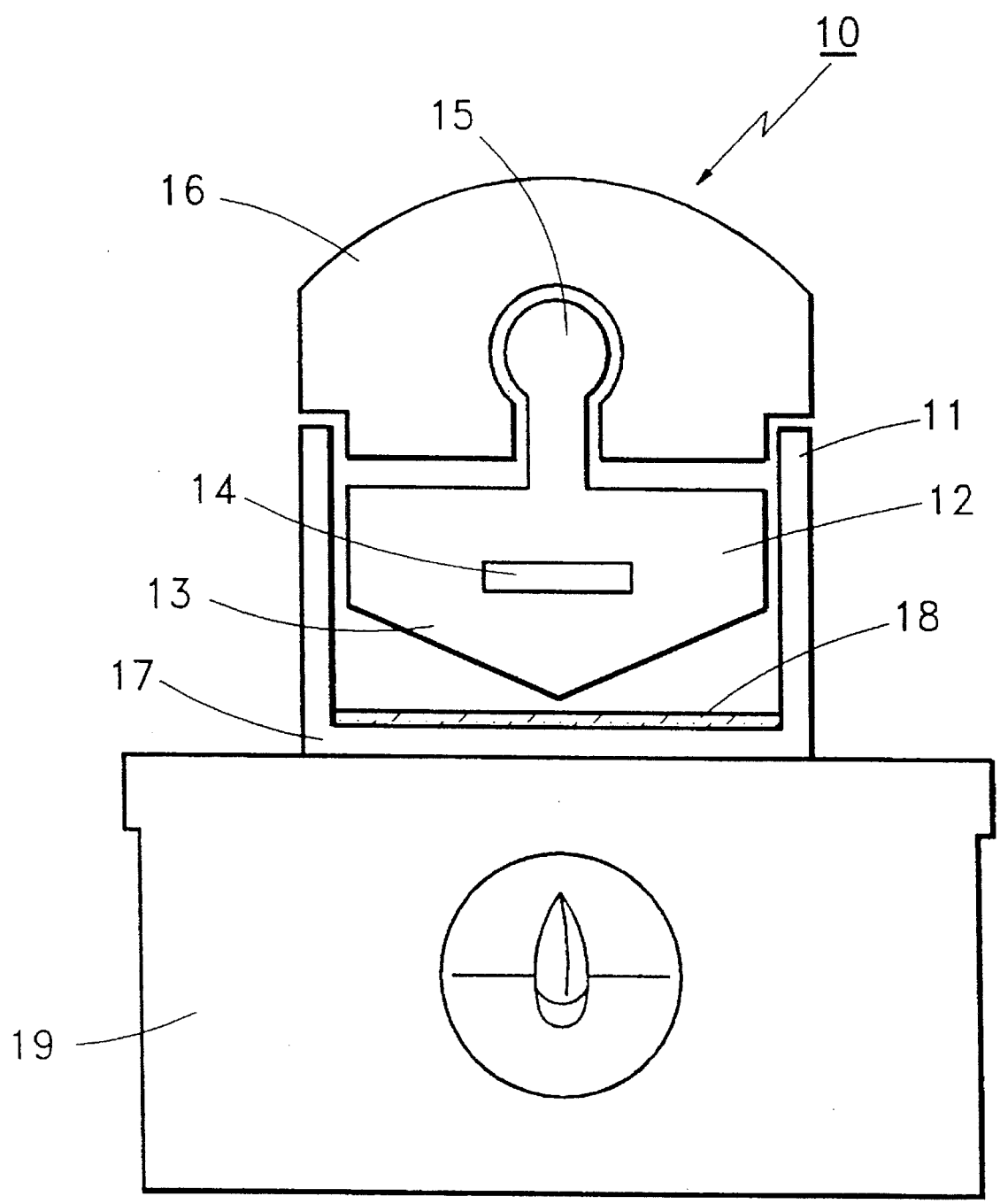
FIG. 1 is a schematic representation of an apparatus of the invention.

Reference is first made to FIG. 1 which is a schematic representation of an apparatus according to one embodiment of the invention. The apparatus in accordance with this embodiment comprises a cone-plate device 10 comprising a cylindrical vessel 11 and a rotating element 12 a bottom portion 13 having the shape of an inverted cone. The rotating element 12 holds inside a magnetic bar 14. The upper portion 15 of the clement 12 is held inside stopper 16, whereby element 12 is suspended from the stopper inside vessel 11 and can rotate freely. The bottom surface 17 of vessel 11 is covered by ECM 18. The device 10 is placed on a magnetic stirrer apparatus 19.

In operation, a blood sample, optionally mixed with an anti-coagulant, is introduced into the vessel 11, and then the stopper 16 with the suspended element 12 is placed on the vessel. The device is then placed on the magnetic stirring apparatus 19, the operation of which creates a rotating magnetic field which cause the rotation of element 12. Consequently, shear forces are produced on the ECM covered surface 18, which is essentially constant throughout the entire surface.

EXAMPLE I

Qualitative Evaluation by Scanning Electron Microscope (SEM)

Whole blood was collected from normal volunteers or patients with an hemostatic disorder, including Glanzman's thrombasthenia (GT), von Willebrand disease (vWD) Afibrinogenemia (AF) and other non-defined abnormalities. Samples were collected also from patients before coronary bypass with apparently increased primary hemostasis who are predisposed to thrombosis.

To each sample, 0.38% of sodium citrate which acts as an anti-coagulant, was added.

200 μl–500 μl of the citrated blood was added to the apparatus described above with or without pre-incubation with blockers or their controls.

The sample was subjected to a low or high shear force for 2 min, by selecting the corresponding speed of the rotating disk: for low shear force the sample was rotated at a speed of 100–200 rpm, and for high shear force, the sample was rotated at a speed of 1000–2000 rpm. In the specific setting the rotating speed (rpm) corresponded exactly to the shear force which was applied (in units of $sec^{-1}$).

The sample was then washed by phosphate buffered saline and the evaluation of the level of adherence and aggregation on the ECM was carried out by examination under a scanning electron microscope (SEM).

Figure 2:
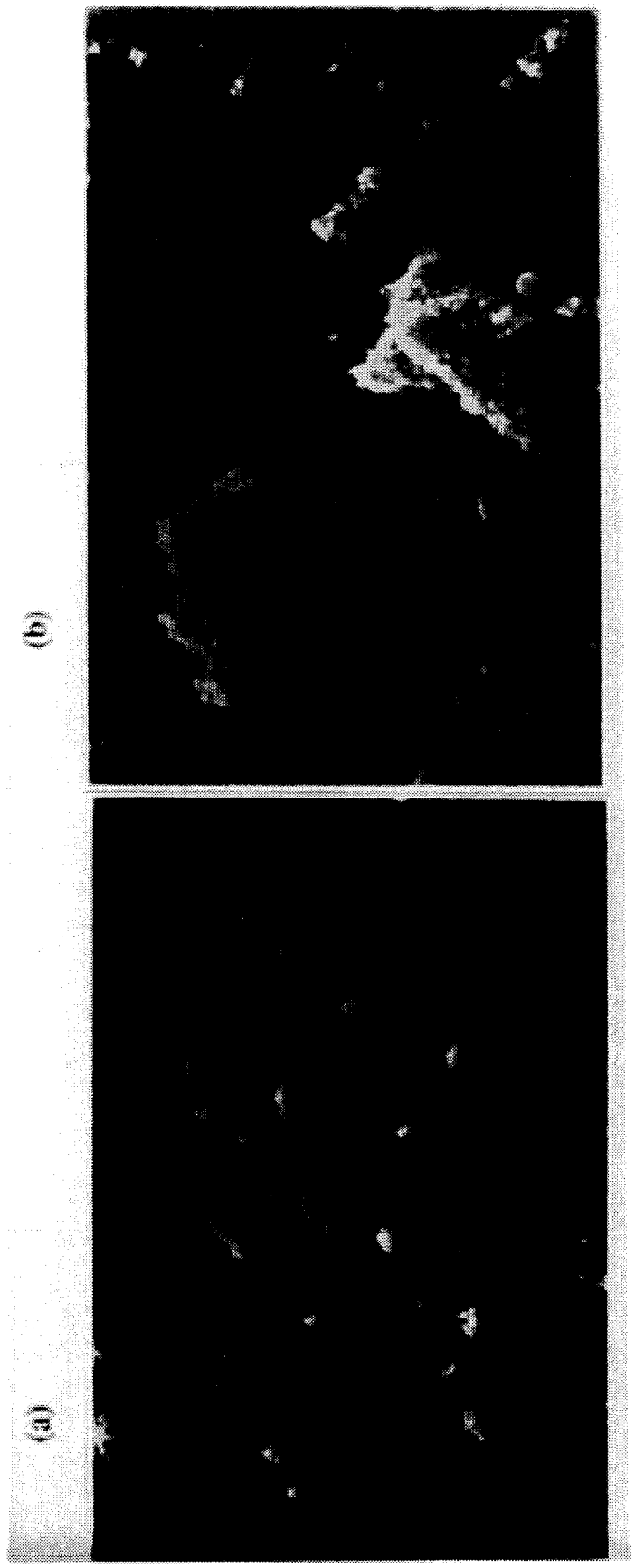
FIGS. 2A–B show a scanning electron microscope (SEM) picture depicting the formation of aggregate adhered to ECM in control blood (magnification: ×745) under low (l) and high (h) shear force conditions.

FIG. 2 shows SEM pictures of normal blood samples tested under low (l) shear force conditions (100 $sec^{-1}$) and under high (h) shear force conditions (1000 $sec^{-1}$). As can be seen, normal blood showed a reproducible mode of adherence/aggregation in both of the shear forces employed.

When blood from different patients with hemostatic abnormalities was tested in the hemostatometer a clear decrease in both the adhesion and the aggregation rate was observed. The following are some examples of such testings:

Glanzmann Thrombasthenia (GT) (FIG. 3)—There was a total lack of aggregate formation in both low (l) and high (h) shear force and the single adhered platelets were only partially spread, exhibiting some pseudopodia formation.

von Willebrand Disease (vWD) (FIG. 4)—There was no aggregate formation in both high (h) and low (l) shear force conditions and the adhered platelets are exhibiting partial spreading (comparable to the spreading of normal platelets on a plastic surface).

The pathologic aggregation of vWd platelets could partially be corrected by either in vitro or in vivo treatment with vWF (data not shown).

Afibrinogenemia (AF) (FIG. 5)—Afibrinogenemic platelets present a pathologic interaction with the ECM with some pseudopodia formation of the single adhered platelets. While absolute no aggregate formation was found in the low (l) shear conditions experiment, there was a definite aggregation when high (h) shear force was applied. These data were in accordance with the concept that at high (h) shear conditions (which correspond to arterial conditions) vWF is the major interaction ligand that mediate platelets with ECM and platelet-plalelet interaction.

Specific Receptor Blockers (FIG. 6)—The application of both a vWF fragment which serves as a vWF blocker (VWFf) and the Integrin receptor blocker Arginine-Glycine-Aspwotic-Serin tetra peptide (RGDS) at concentrations of 4 μM and 15 μM, respectively, under high shear force conditions in the apparatus of the invention created pathologic interaction of platelets with ECM. The effect of the specific receptor blockers was comparable to the corresponded diseases vWD and GT, respectively.

EXAMPLE II

Quantitative Evaluation by an Image Analysis System (IAS)

Normal platelets in citrated whole blood were circulated over ECM, using the device represented in FIG. 1 at varying degrees of shear rates as indicated below. The shearing action was applied for various periods of time ranging from 15 seconds to 5 mins.

The ECM surfaces were then examined by an IAS. The parameters that could be evaluated in the system included:

(i) percentage of total area covered by adhered platelet aggregation (which is designated in graphs shown below as percent surface coverage);

(ii) mean size of observed objects (indicated in the graph below as "mean particle size");

(iii) percentage of single adhered/spread platelets (mean area of 5–6 $\mu m^2$);

(iv) percentage of platelet aggregates (aggregates having a mean area larger than 14 $\mu m^2$).

Figure 7A:
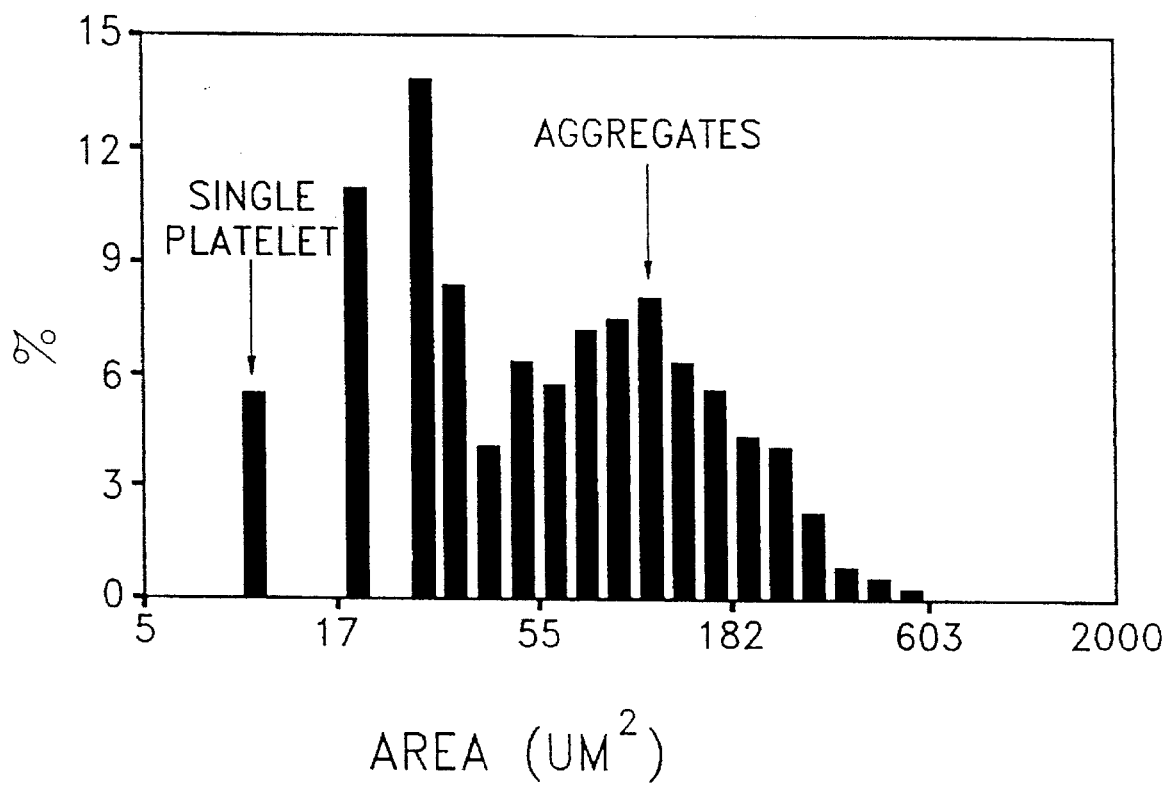
FIGS. 7A–C show a particle size histogram of representative results, obtained by image analysis, of size of platelet aggregates adhered to ECM of blood from normal subjects (A), subjects suffering from von Villebrand's disease (B) and from subjects having Glanzmann's Thrombasthenia (C)
Figure 7B:
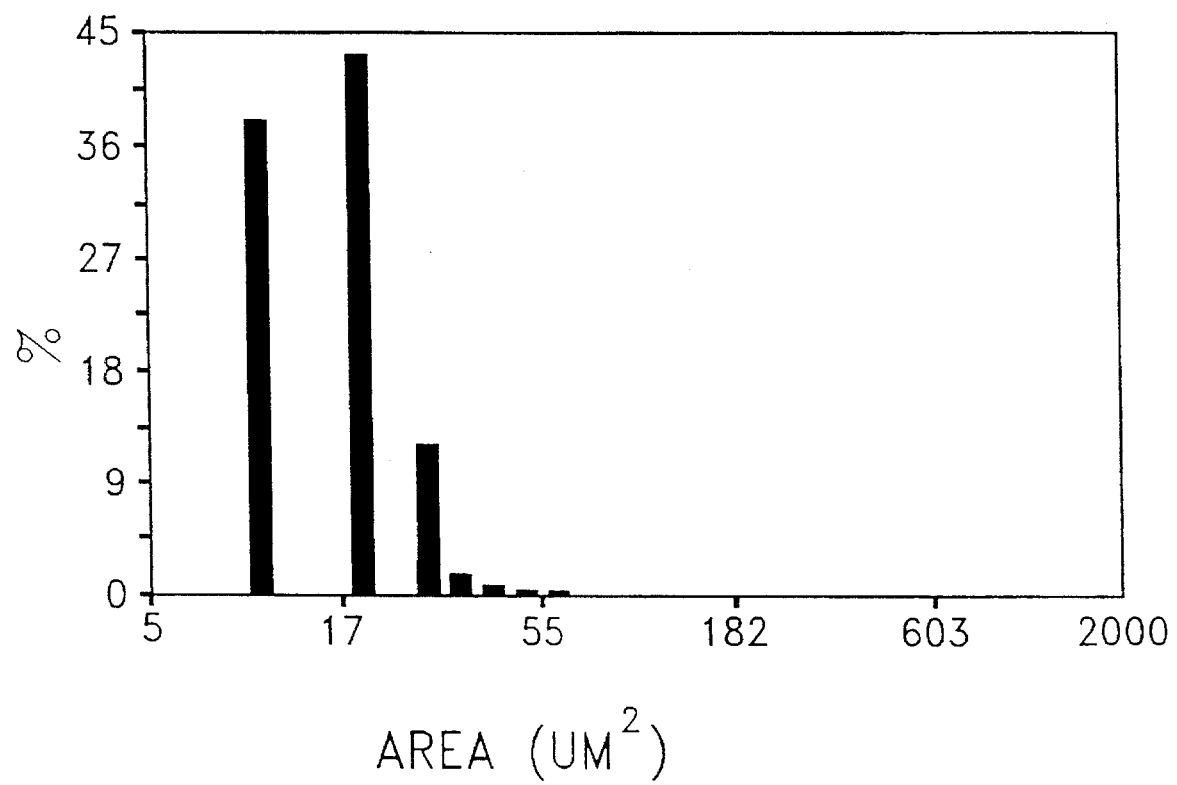
Figure 7C:
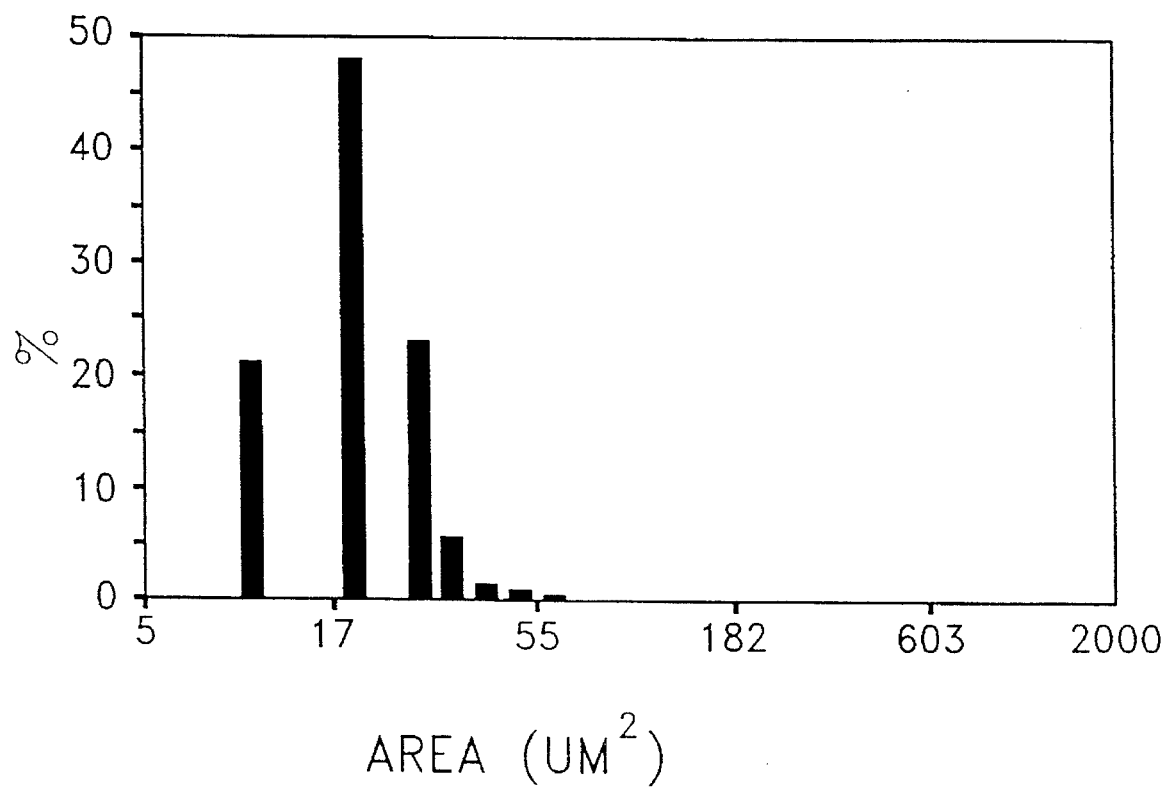

FIG. 7 shows representative results from three cases: normal subjects (A), subjects suffering from von Willebrand's Disease (B) and subjects suffering from Glanzmann's Thrombasthenia (C). As can be seen in diseased subjects, there was a dramatic reduction in all the above four parameters, except the percentage of the single adhered platelets (the first column in the histogram).

The results obtained from normal subjects in patients of various diseases are summarized in the following Table 1:

TABLE I

| | Surface Coverage (% total area) | Mean size (mm²) | % Single platelets | % Aggregates >40 μm² |
|---|---|---|---|---|
| Control 100s⁻¹ | 9.5 ± 1.7 | 24.1 ± 2.3 | 51.7 ± 8.7 | 12.8 ± 3.3 |
| Control 1500s⁻¹ | 20.1 ± 6.7 | 42.3 ± 11.8 | 37.7 ± 9.3 | 37.0 ± 6.5 |
| vWD 100s⁻¹ | 5.3 ± 1.7 | 13.8 ± 1.3 | 87.0 ± 2.0 | 0 |
| vWD 1500s⁻¹ | 3.7 ± 0.1 | 12.5 ± 0.1 | 92.0 ± 1.3 | 0 |
| GT 100s⁻¹ | 3.9 ± 1.8 | 10.5 ± 1.2 | 92.0 ± 3.0 | 0 |
| GT 1500s⁻¹ | 1.8 ± 0.5 | 12.6 ± 0.2 | 92.0 ± 1.0 | 0 |
| AF 100s⁻¹ | 4.4 | 14.2 | 83 | 0 |
| AF 1500s⁻¹ | 8.5 | 24.9 | 64 | 10 |

As can be seen from the above table, the difference between normal and control is apparent in all tested parameters and the observed changes are apparent following applications of both low ($100s^{-1}$) or high ($1500s^{-1}$) shear rates.

Figure 8:
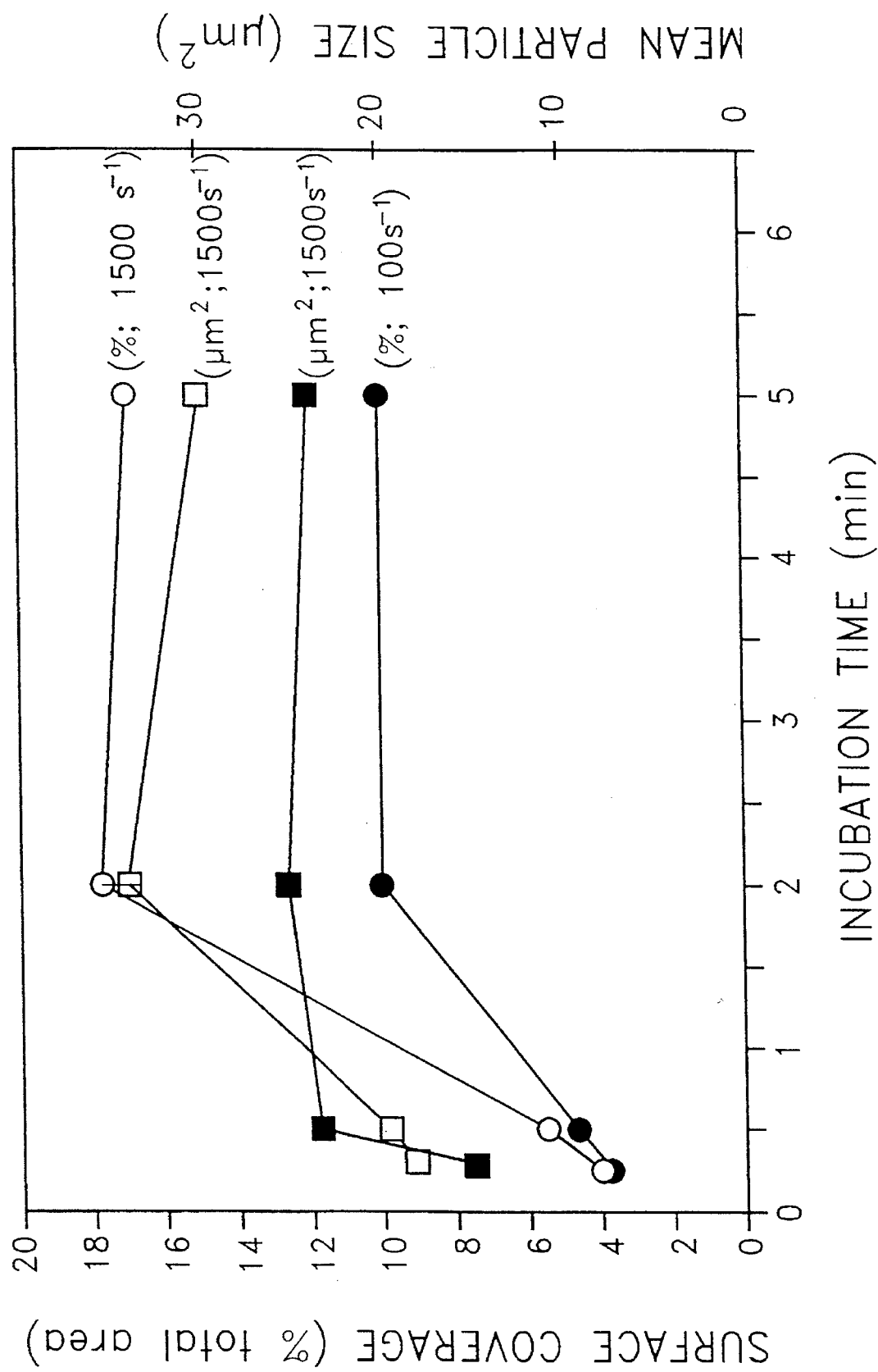
FIG. 8 shows the surface coverage and the mean aggregate size of platelet particles (either single or aggregated) adhered onto the ECM surface as a function of incubation time under either low (100 $sec^{-1}$) or high (1000 $sec^{-1}$) shear conditions.

The time course of platelet deposition at both low and high shear rate is shown in FIG. 8. As can be seen, the deposition progresses with time, as evidenced both by the increase in surface coverage and in the mean particle size. Furthermore, as can be seen, at both shear rates, there was a time dependent increase in the percentage of surface coverage as well as in the mean size of ECM-bound particles (mean particle size). Maximum values of surface coverage in mean aggregate size were obtained after about 2 mins. of blood circulation at both low and high shear rate conditions.

Figure 9:
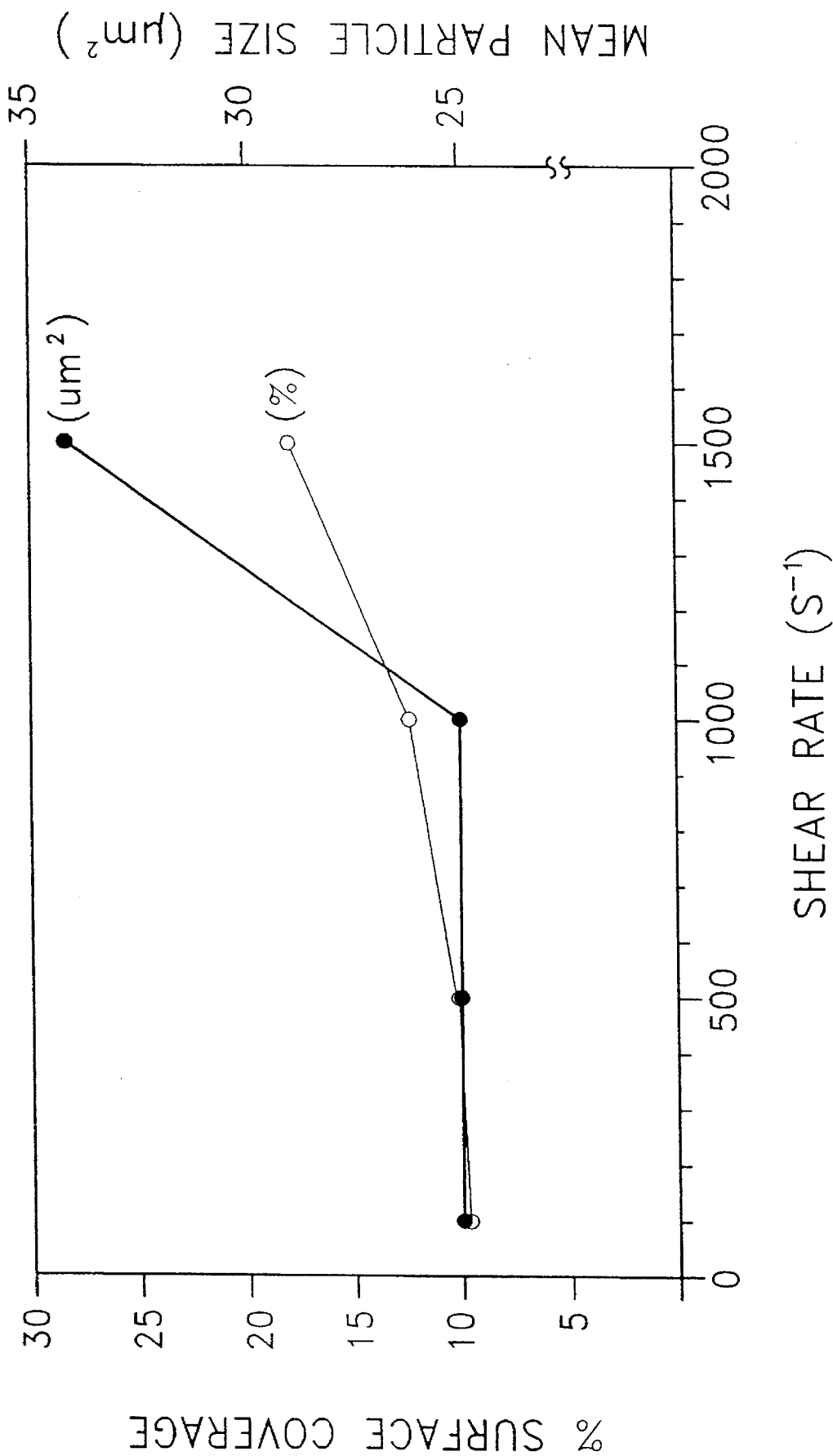
FIG. 9 shows the surface coverage and the mean aggregate size of platelet particles (either single or aggregated) adhered onto the ECM surface as a function of the shear rate.

The rate of platelet deposition on ECM (% surface coverage and mean particle size) as a function of shear rate (shear force applied for 1 min.) is shown in FIG. 9. As can be seen, there is no significant variation in the percentage of surface coverage or in the mean aggregate size between shear rate of 100 to 1000 $sec^{-1}$. However, at 1500 $sec^{-1}$, a significant increase in both parameters can be observed.

On the basis of the time course and shear rate dependence experiments, optimal conditions can be chosen: circulation period of about 2 mins, which was found to be sufficient to achieve maximal surface coverage and maximal mean aggregate size at both high and low shear rates; a choice of 100 $sec^{-1}$ as a low shear rate and a 1500 $sec^{-1}$ as a high shear rate.

Normal platelets in the citrated whole blood were circulated over ECM for 2 mins. at either high or low shear rate. At both shear rates, platelets adhered and aggregated onto this ECM. The extent of aggregation, however, was significantly higher at the high shear rate. Incubation of whole blood with ECM at high shear rate yielded aggregates which were much larger than those formed under low shear conditions (see FIG. 9 and Table I). The percentage of large aggregates (>40 μm²) formed at high shear rate was 37.0%±6.54%, as compared to 12.83%±3.25% at the low shear rate. The higher extent of platelet aggregation at the high shear rate was also reflected by the larger mean size of ECM-bound particles (42.26±11.78 μm² at high shear rate, as compared to 24.06±2.34 μm² at low shear rate), as well as by a higher percentage of surface coverage (see Table I).

Figure 3:
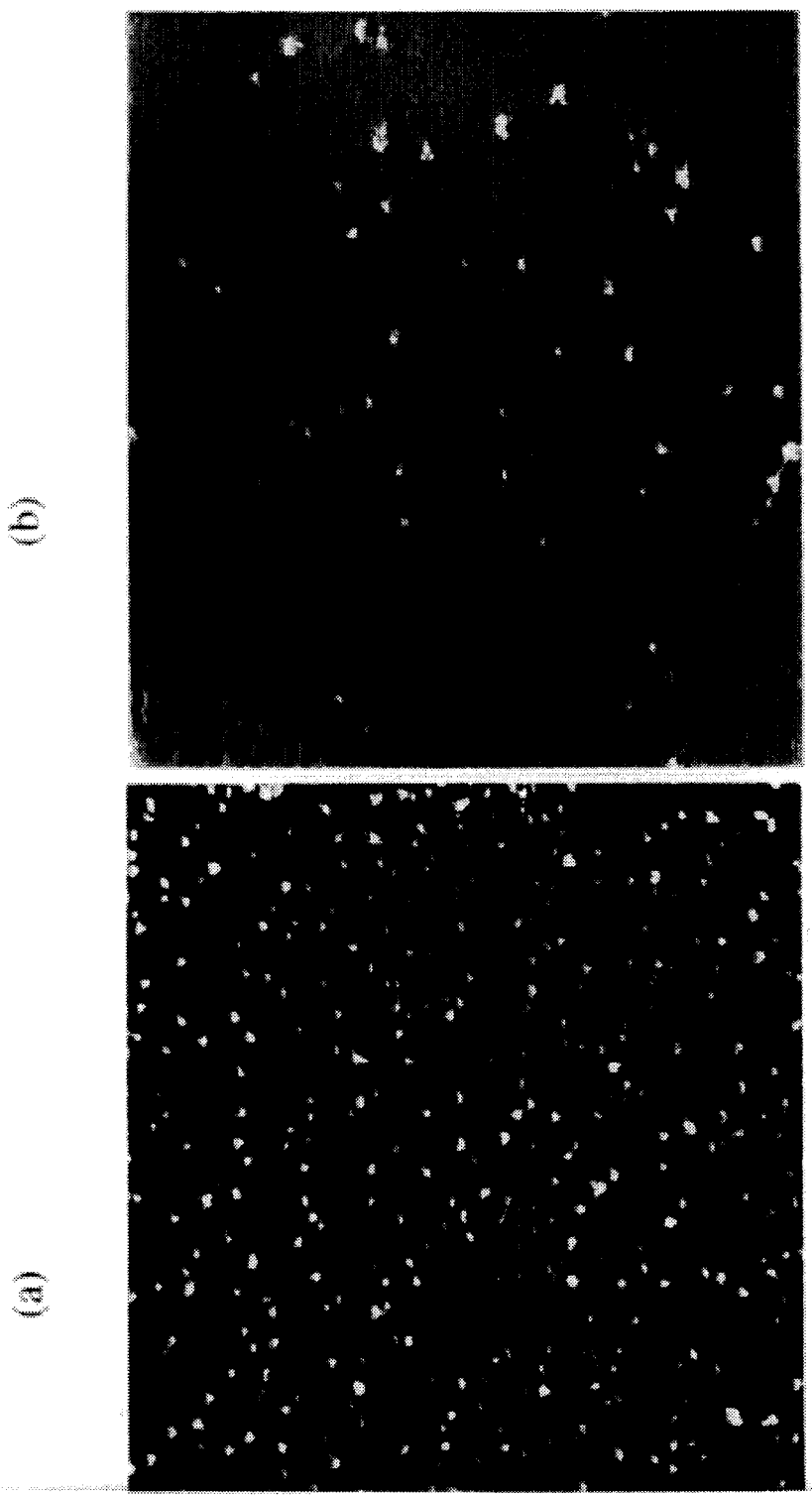
FIGS. 3A–B show an SEM picture depicting the formation of aggregate adhered to ECM in blood of patients suffering from Glanzmann's Thrombasthenia (magnification: ×745) under low (l) and high (h) shear force conditions.
Figure 4:
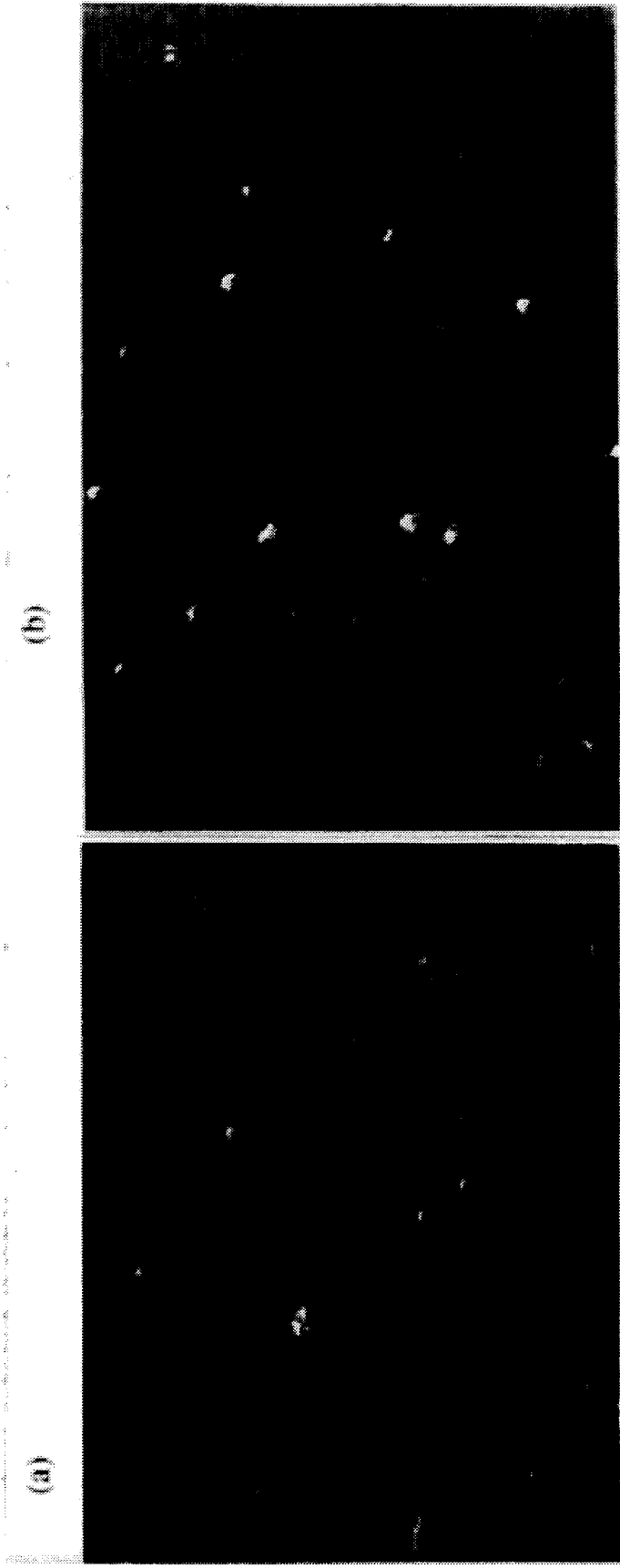
FIGS. 4A–B show an SEM picture depicting the formation of aggregate adhered to ECM in blood of patients suffering from von Willebrand's disease (magnification: ×1000) under low (l) and high (h) shear force conditions.

Incubation on ECM of citrated whole blood taken from either type III vWD patient or a GT patient resulted in limited platelet adhesion without aggregation at both high and low shear rates (FIGS. 3 and 4, as well as Table I). At both low and high shear rates, surface coverage, as well as the mean size of ECM-bound particles were greatly reduced in both vWD and GT samples, when compared to the corresponding normal control values. Both vWD and GT samples have demonstrated a more pronounced decrease in surface coverage when high shear rate conditions were applied.

Figure 5:
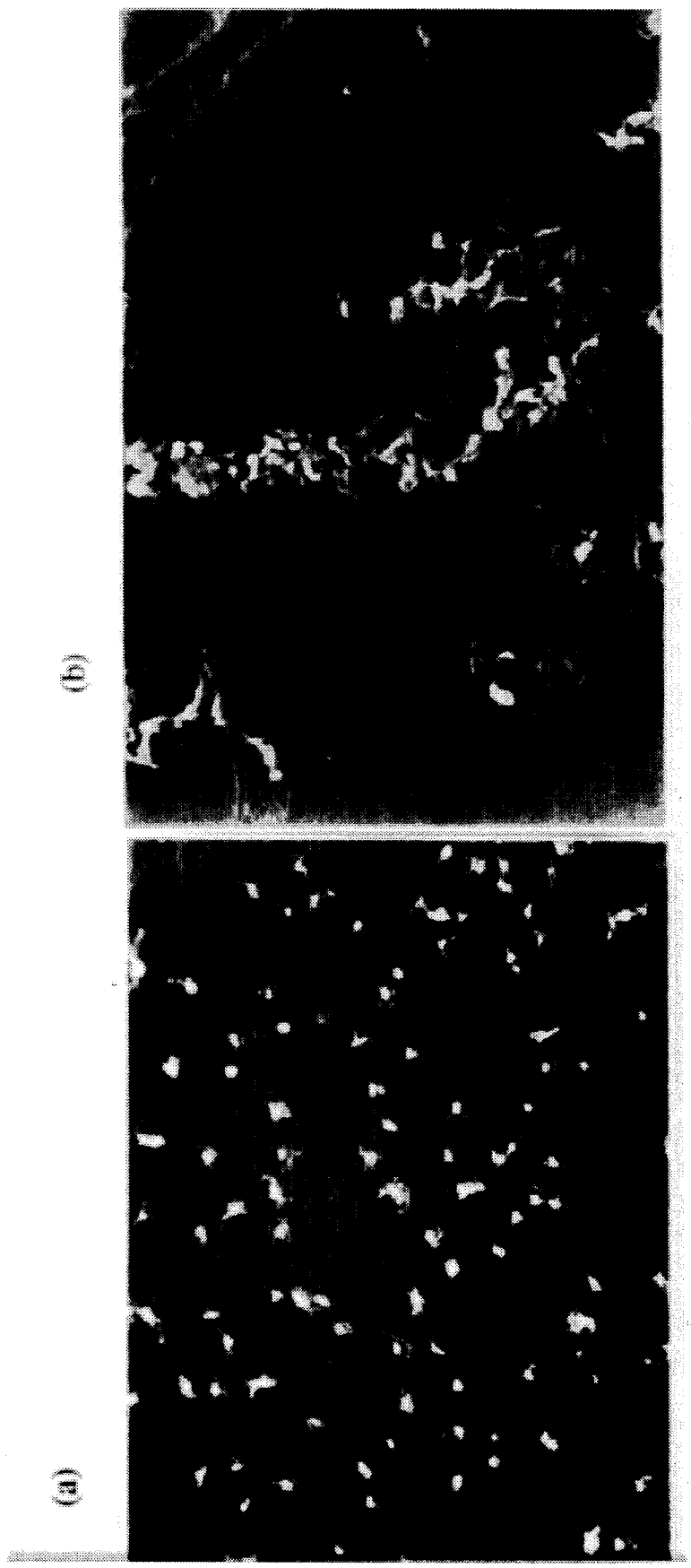
FIGS. 5A–B show an SEM picture depicting the formation of aggregate adhered to ECM in blood of patients suffering from Afibrinogenemia (magnification: l–×1000; h–×1700) under low (l) and high (h) shear force conditions.

Under low shear conditions, platelets in fibrinogen deficient blood exhibited adhesion to ECM without aggregate formation (see FIG. 5 and Table I). In contrast, at high shear rate, both adhesion and aggregation could be observed. The parameters of platelet deposition on ECM obtained from Afibrinogenemic blood under high shear rate conditions were very similar to those observed in control samples at low shear rate (see Table I). These findings are in agreement with previous reports showing that platelet aggregation can occur in the absence of fibrinogen at high, but not at low shear conditions.

Figure 10A:
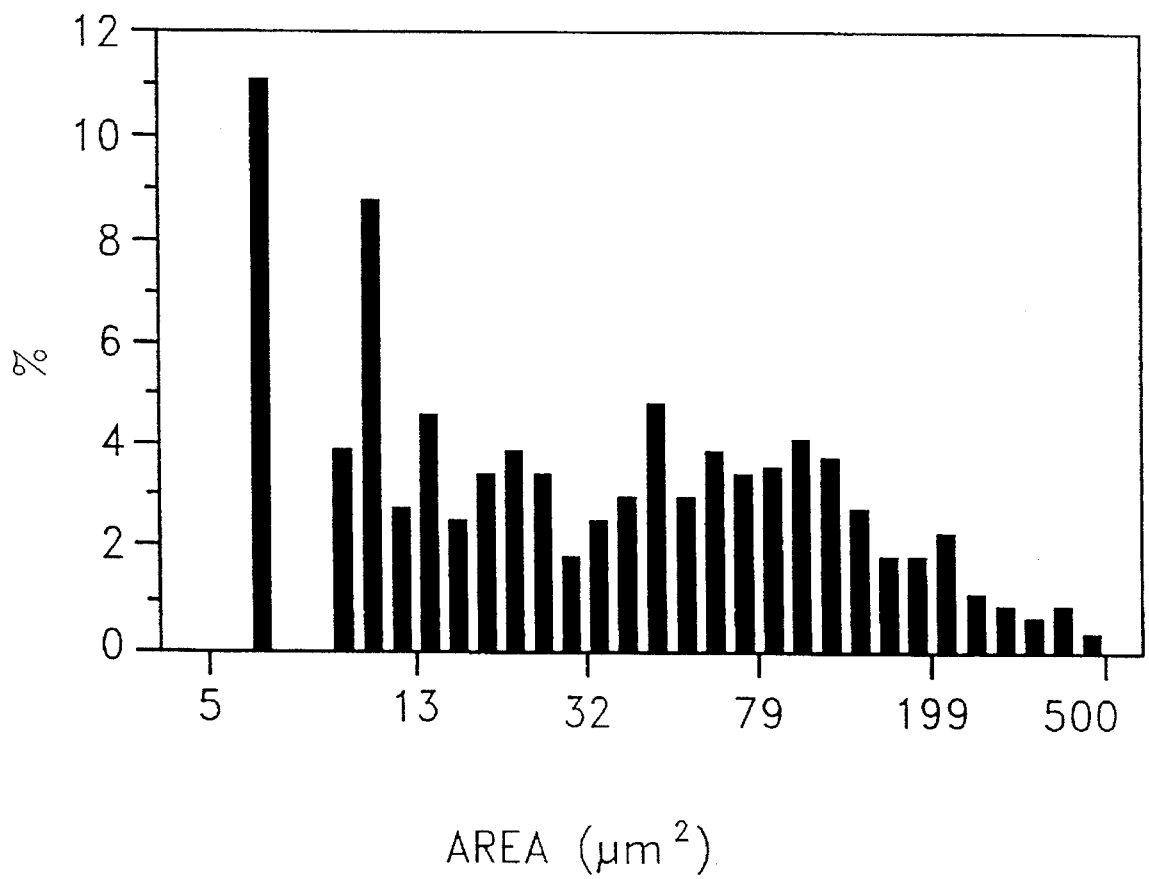
FIGS. 10A–C show particle size histograms of platelet particles adhered onto the ECM surface from blood from patients before coronary angioplastic (A), blood from normal subjects (B) and blood from patients under asperin therapy (C).
Figure 10B:
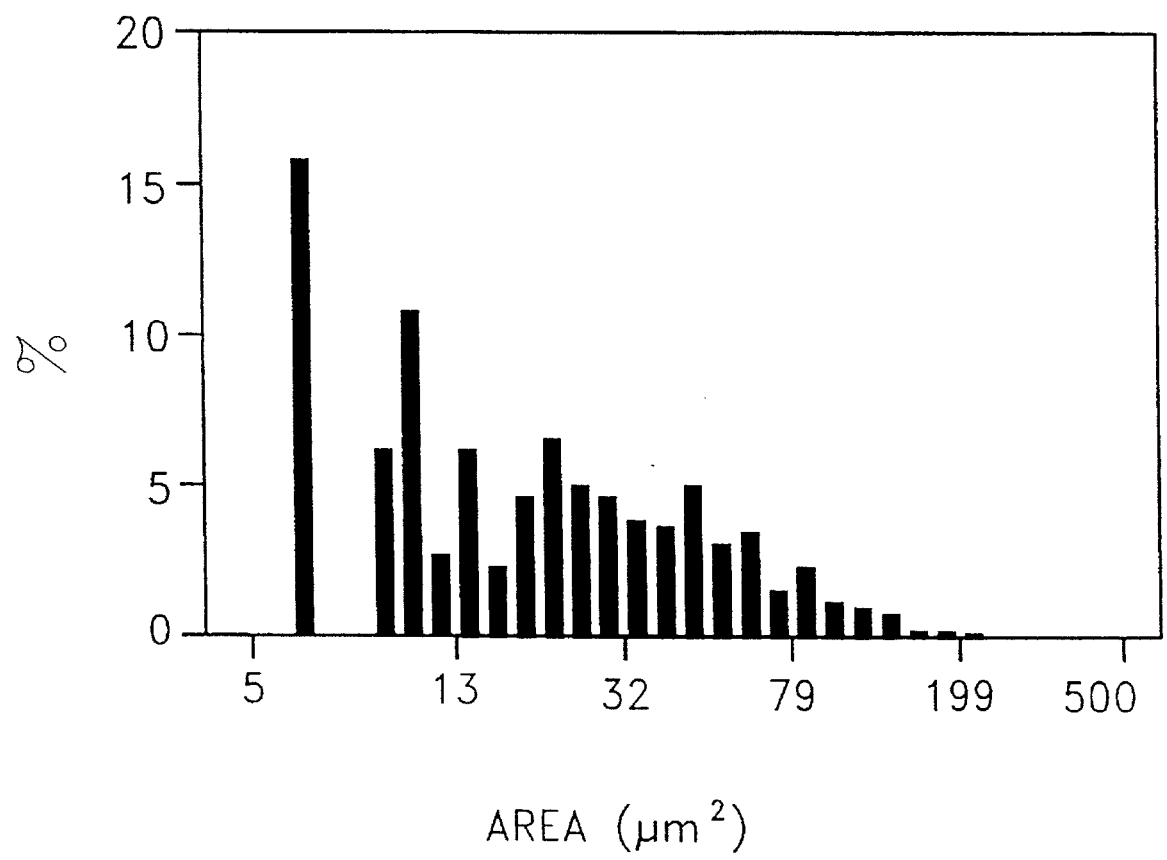
Figure 10C:
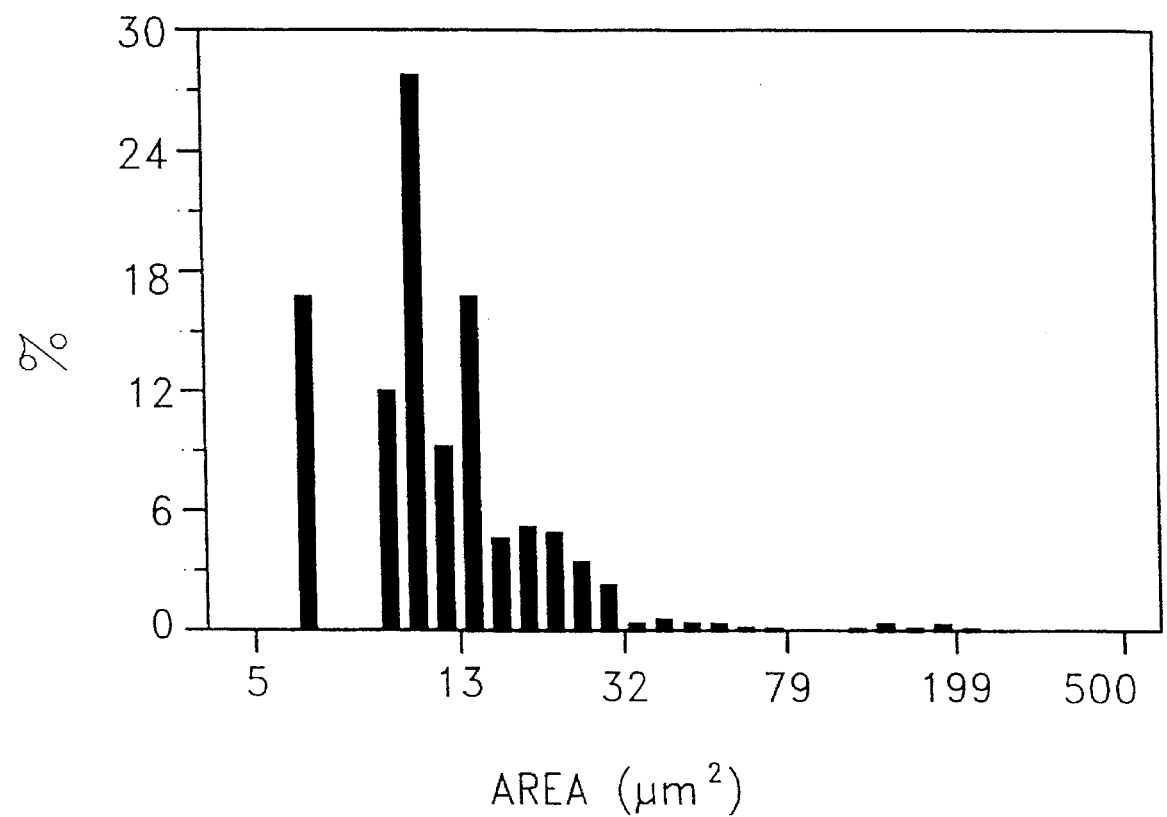

The potential of the method of the invention to identify hyperactive hemostasis (and prethrombotic state) is demonstrated in FIG. 10. This figure shows an IAS evaluation of normal subjects (middle panel), patients under aspirin therapy (lower panel) and patients before coronary angioplasty (upper panel). As can be seen, there is a clear difference in all parameters between the different panels, suggesting a higher adhesion and aggregation rate in the coronary heart disease patient and a reduced adhesion in the aspirin treated patients.

We claim:

1. A method for determining platelet function in primary hemostasis comprising:
   (a) obtaining a sample being whole-blood or a platelet-containing fraction thereof;
   (b) introducing the sample obtained in (a) into a vessel having a flat bottom, an inner surface of which is covered with a substrate capable of inducing platelet adhesion thereto and aggregation;
   (c) rotating said sample inside the vessel, whereby shear forces develop at said inner surface; thereby causing adherence and aggregation of blood platelets onto said inner surface;
   (d) determining parameters of the adhered and aggregated blood platelets, the parameters being selected from the group consisting of amount of adhered platelets, aggregate size, aggregates' morphology, total area covered by the aggregates and distribution of adhered platelets or aggregates.

2. A method according to claim 1, wherein said substrate is Extracellular matrix or an active component thereof capable of inducing platelet adhesion thereto and aggregation.

3. A method according to claim 2, wherein said substrate is said active component of said extracellular matrix and said active component is selected from the group consisting of: basement membrane matrix, fibrillar and non-fibrillar collagen of various types, von Willebrand factor and fibronectin.

4. A method according to claim 1, wherein the vessel has a cylindrical rotating element located therein.

5. A method according to claim 1, wherein the vessel has a rotating element located therein which has a bottom portion having the shape of an inverted cone.

6. A method according to claim 1, wherein the sample is mixed with an anti-coagulant in an amount sufficient to inhibit blood coagulation prior to introduction into the vessel.

7. An apparatus for determining platelet function in primary hemostasis, comprising a flat-bottomed vessel capable of receiving liquids and a rotating element placed within said flat-bottomed vessel, wherein the inner face of the bottom of said vessel is lined with a substrate capable of inducing platelet adhesion thereto and aggregation.

8. An apparatus according to claim 7, wherein the rotating element has an essentially conical shape.

9. An apparatus according to claim 8, in which the angles of the conical rotating element are adjusted so that during rotational movements thereof the shear force produced through the bottom inner face of the vessel is essentially equal.

10. An apparatus according to claim 7 wherein said substrate is extracellular matrix or an active component thereof capable of inducing platelet adhesion thereto and aggregation.

11. An apparatus according to claim 10, wherein the active component of the extracellular matrix is selected from the group consisting of basement membrane matrix, fibrilar and non-fibrilar collagen of various types, von Willebrand factor and fibronectin.

* * * * *

UNITED STATES PATENT AND TRADEMARK OFFICE
CERTIFICATE OF CORRECTION

PATENT NO. : 5,523, 238
DATED : June 4, 1996
INVENTOR(S) : Varon, et al.

It is certified that error appears in the above-indentified patent and that said Letters Patent is hereby corrected as shown below:

| | |
|---|---|
| Col. 2, line 22 | Delete " lo " and substitute -- to -- |
| Col. 2, line 45 | After " platelets " insert -- , -- |
| Col. 3, line 62 | Delete " fiat " and substitute -- flat -- |
| Col. 4, line 26 | After " FIGS. 2 " delete " A-B " and substitute -- (a)-(b) -- |
| Col. 4, line 28 | Delete " (I) " and substitute -- (a) -- |
| Col. 4, line 29 | Delete " (h) " and substitute -- (b) -- |
| Col. 4, line 30 | After " FIGS. 3 " delete " A-B " and substitute -- (a)-(b) -- |
| Col. 4, line 34 | Delete " low (I) and high (h) " and substitute -- low (a) and high (b) -- |
| Col. 4, line 35 | After " FIGS. 4 " delete " A-B " and substitute -- (a)-(b) -- |
| Col. 4, line 38 | Delete " low (I) and high (h) " and substitute --low (a) and high (b) -- |
| Col. 4, line 39 | After " FIGS. 5 " delete " A-B " and substitute -- (a)-(b) -- |
| Col. 4, line 41 | Delete " I-x1000 " and substitute -- a-x1000 -- |

UNITED STATES PATENT AND TRADEMARK OFFICE
CERTIFICATE OF CORRECTION

PATENT NO. : 5,523,238
DATED : June 4, 1996
INVENTOR(S) : Varon, et al.

Figure 6:
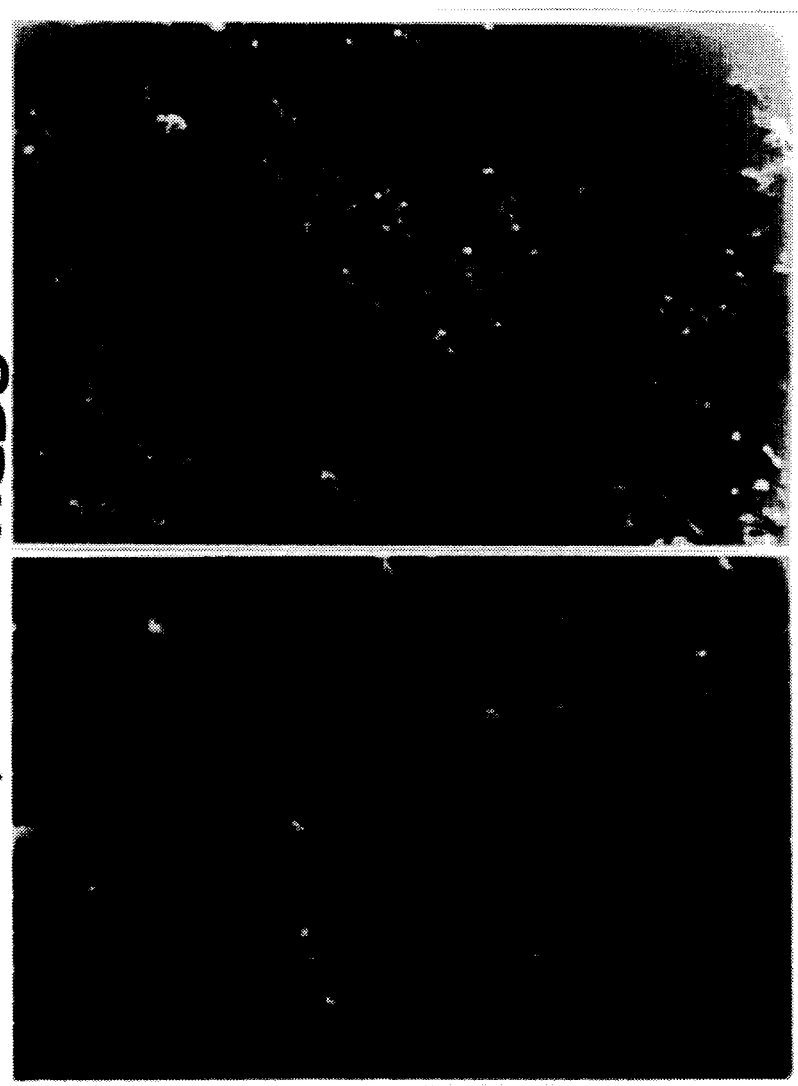
FIGS. 6A–B show an SEM picture depicting the formation of aggregate adhered to ECM in tested blood samples supplied with (A) von Willebrand's blockers (VWFf) and (B) integrin receptor blockers (RGDS) (magnification: $vWF_f$ –×745; RGDS–×1500)

It is certified that error appears in the above-indentified patent and that said Letters Patent is hereby corrected as shown below:

| | |
|---|---|
| Col. 4, line 42 | Delete " h-x1700 " and substitute -- b-x1700 -- |
| Col. 4, line 42 | Delete " low (I) and high (h) " and substitute -- low (a) and high (b) -- |
| Col. 4, line 43 | After " FIGS. 6 " delete " A-B " and substitute -- (a)-(b) -- |
| Col. 4, line 45 | Delete " (A) " and substitute -- (a) -- |
| Col. 4, line 46 | Delete " (B) " and substitute -- (b) -- |
| Col. 4, line 47 | Delete " $vWF_f$ " and substitute -- vWFf -- |
| Col. 4, line 51 | Delete " vonVillebrand's " and substitute -- vonWillebrand's |
| Col. 5, line 46 | Delete " 100-200 rpm " and substitute -- 40-100 rpm -- |
| Col. 5, line 47 | Delete " 1000-2000 rpm " and substitute -- 300-1000 rpm -- |
| Col. 5, line 49 | After " (rpm) " delete " corresponded exactly to " and substitute -- multiplied by 25 to give -- |
| Col. 5, line 56 | After " low " delete " (I) " and substitute -- (a) -- |

UNITED STATES PATENT AND TRADEMARK OFFICE
CERTIFICATE OF CORRECTION

PATENT NO.   : 5,523,238
DATED        : June 4, 1996
INVENTOR(S)  : Varon, et al.

It is certified that error appears in the above-indentified patent and that said Letters Patent is hereby corrected as shown below:

| | |
|---|---|
| Col. 5, line 57 | After " high " delete " (h) " and substitute -- (b) -- |
| Col. 5, line 61 | Delete " hemostatomerer " and substitute -- apparatus -- |
| Col. 6, line 2 | After " low " delete " (I) " and substitute -- (a) -- |
| Col. 6, line 3 | Delete " (h) " and substitute -- (b) -- |
| Col. 6, line 6 | Delete " (h) and low (I) " and substitute -- (b) and low (a) -- |
| Col. 6, line 10 | Delete " vWd " and substitute -- vWD -- |
| Col. 6, line 17 | After " low " delete " (I) " and substitute -- (a) -- |
| Col. 6, line 18 | After " high " delete " (h) " and substitute -- (b) -- |
| Col. 6, line 19 | After " high " delete " (h) " and substitute -- (b) -- |
| Col. 6, line 26 | Delete " Aspwotic-Serin " and substitute -- Aspartic-Serine -- |
| Col. 6, line 43 | After " then " insert -- washed, fixed, stained, "; after " by " delete " an " and substitute -- a light microscope analyzed by -- |

UNITED STATES PATENT AND TRADEMARK OFFICE
CERTIFICATE OF CORRECTION

PATENT NO. : 5,523,238
DATED : June 4, 1996
INVENTOR(S) : Varon, et al.

It is certified that error appears in the above-indentified patent and that said Letters Patent is hereby corrected as shown below:

Col. 6, line 52   Delete " $5\text{-}6\mu m^2$ " and substitute -- $5\text{-}20\mu m^2$ --

Col. 6, line 54   Delete " $14\mu m^2$ " and substitute -- $20\mu m^2$ --

Col. 6, line 62   After " subjects " insert -- and --

Col. 7, TABLE 1   Third Column after " Mean size " delete $mm^2$ " and substitute -- $\mu m^2$ --

Signed and Sealed this

Twenty-fourth Day of June, 1997

Attest:

Attesting Officer

BRUCE LEHMAN

Commissioner of Patents and Trademarks